United States Patent [19]

Chandrasekaran et al.

[11] 4,201,211
[45] May 6, 1980

[54] THERAPEUTIC SYSTEM FOR ADMINISTERING CLONIDINE TRANSDERMALLY

[75] Inventors: Santosh K. Chandrasekaran, Palo Alto, Calif.; Siegfried Darda, Ingelheim am Rhein, Fed. Rep. of Germany; Alan S. Michaels, Atherton; Gary W. Cleary, Palo Alto, both of Calif.

[73] Assignees: ALZA Corporation, Palo Alto, Calif.; Boehringer Ingelheim GmbH, Ingelheim am Rhein, Fed. Rep. of Germany

[21] Appl. No.: 815,033

[22] Filed: Jul. 12, 1977

[51] Int. Cl.$^2$ .............................................. A61F 7/02
[52] U.S. Cl. .................................................... 128/268
[58] Field of Search ...................... 128/156, 260, 268; 424/19, 20, 28

[56] References Cited

U.S. PATENT DOCUMENTS

| | | | |
|---|---|---|---|
| 3,190,802 | 6/1965 | Zeile et al. ............................... | 424/73 |
| 3,202,660 | 8/1965 | Zeile et al. ............................... | 260/254 |
| 3,454,701 | 7/1969 | Zeile et al. ............................... | 424/273 |
| 3,598,122 | 8/1971 | Zaffaroni ................................. | 128/268 |
| 3,666,861 | 5/1972 | Zaimis et al. ........................... | 424/273 |
| 3,731,683 | 5/1973 | Zaffaroni ................................. | 128/156 |
| 3,742,951 | 7/1973 | Zaffaroni ................................. | 128/268 |
| 3,797,494 | 3/1974 | Zaffaroni ................................. | 128/268 |
| 3,972,995 | 8/1976 | Tsuk et al. .............................. | 128/156 |
| 4,031,894 | 6/1977 | Urquhart et al. ...................... | 128/268 |

OTHER PUBLICATIONS

Klin. Mbl. Augenheilk., 160 (1972) 188.
Klin. Mbl. Augenheilk., 161 (1972) 73.

*Primary Examiner*—Robert W. Michell
*Assistant Examiner*—C. F. Rosenbaum
*Attorney, Agent, or Firm*—Thomas E. Ciotti; Paul L. Sabatine; Edward L. Mandell

[57] ABSTRACT

Therapeutic system in the form of a skin patch that administers clonidine transdermally in an initial priming dose of 10 to 300 mcg/cm$^2$ of skin that brings the concentration of clonidine in the blood to a level sufficient to elicit alpha-adrenergic stimulation without intolerable side effects, followed by a substantially constant continuous dosage in the range of 0.1 to 100 mcg/hr that maintains said level. The system is a four-layer laminate of, from the top: a protective backing; a gelled, mineral oil-polyisobutene-clonidine reservoir lamina that is the source of the clonidine for the continuous constant dosage; a microporous membrane that controls the constant dosage rate; and a gelled, mineral oil-polyisobutene-clonidine contact adhesive layer that is the source of the clonidine for the priming dose and the means by which the system is attached to the skin.

14 Claims, 1 Drawing Figure

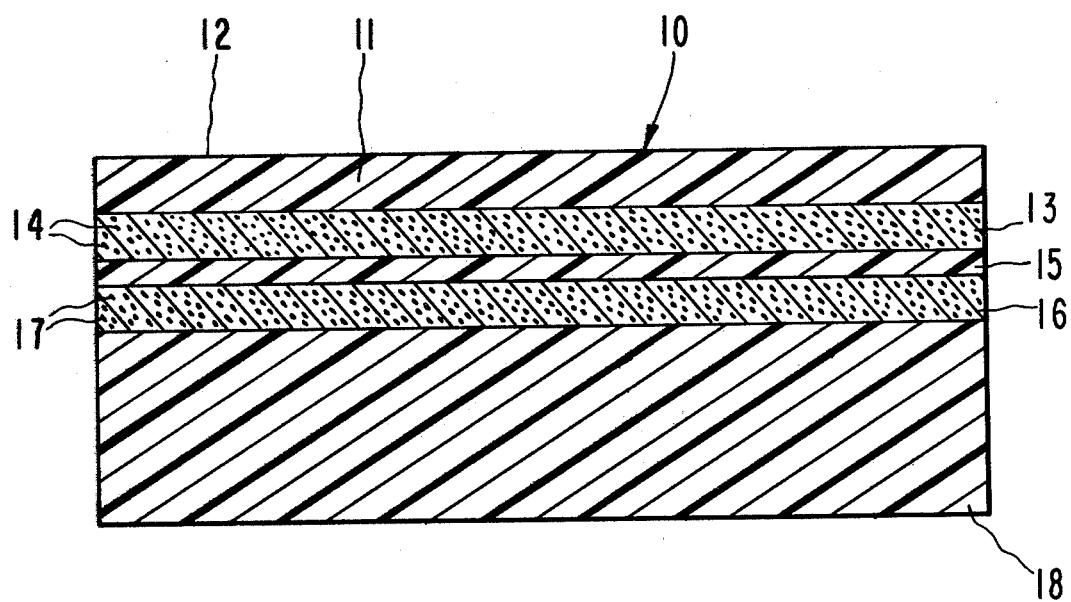

THERAPEUTIC SYSTEM FOR ADMINISTERING CLONIDINE TRANSDERMALLY

BACKGROUND OF THE INVENTION

1. Field of the Invention

This invention relates to a therapeutic system for administering clonidine via intact skin to the systemic circulation to effect alpha-adrenergic stimulation, such as for treating hypertension.

2. Description of the Prior Art

There are several patents/patent applications that relate to bandages or skin patches for administering drugs transdermally to the systemic circulation. In this regard U.S. Pat. Nos. 3,742,951, 3,797,494 and 4,031,894 are believed to be most relevant.

U.S. Pat. No. 3,742,951 describes a 3-layer system or bandage for administering vasodilators transdermally. The bandage comprises a backing layer, a drug release rate controlling reservoir layer that contains the vasodilator, and a contact adhesive layer by which the bandage is attached to the skin. U.S. Pat. No. 3,797,494 describes a similar bandage for administering systemic drugs transdermally comprising a backing layer, a drug reservoir layer, a microporous membrane that controls the drug release rate, and a contact adhesive layer. U.S. Pat. No. 4,031,894 describes a bandage that is structured similarly to the bandage of U.S. Pat. No. 3,797,494. Its bandage contains scopolamine in the contact adhesive layer as well as in the drug reservoir layer such that the scopolamine is administered in an initial priming dose followed by a continuous, substantially constant dosage for up to seven days.

The skin patch of the present invention is designed specifically to administer clonidine transdermally. In this regard the hypotensive properties of clonidine base, derivatives thereof, and related compounds are known. See U.S. Pat. No. 3,454,701. The patent states that clonidine may be formulated for oral, parenteral (i.e. hypodermic injection), or rectal administration to treat hypertension.

U.S. Pat. No. 3,202,660 indicates clonidine is useful for vasoconstrictor therapy. For use in such therapy it is mixed with inert carriers to adapt it for topical application to mucuous membranes such as the nasal cavity.

U.S. Pat. No. 3,190,802 says that clonidine is also useful as a pilomotor agent in shaving compositions. As such it is applied to facial skin in the form of a shaving lotion, soap, or cream.

Clonidine is also useful for treating migraine as described in U.S. Pat. No. 3,666,861 and for treating glaucoma as described in the literature references E. Edelhauser, V. Nemetz, Klin, Mbl. Augenheilkunde 160 (1972) 188 and R. Jahnke, H.W. Thumm, Klin. Mbl. Augenheilk. 161 (1972) 73.

Many factors bear on the practicability of administering a particular drug transdermally to provide therapy for a given condition. Among other requirements, the drug must not damage the skin over prolonged contact therewith (e.g. affect the skin structure adversely, or cause irritation, allergy, or sensitization). It must not be unduly immobilized by the skin. And, it must be capable of permeating through a relatively small area of skin at a therapeutically effective rate. Clonidine unexpectedly meets these requirements.

SUMMARY OF THE INVENTION

The invention is a therapeutic system in the form of a skin patch for administering clonidine continuously and transdermally through a predetermined area of unbroken skin in a controlled manner for a prolonged time period to effect alpha-adrenergic stimulation comprising: a backing that is substantially impermeable to clonidine, one face of which forms the top of the patch; a clonidine reservoir adjacent the opposite face of the backing that contains an amount of clonidine sufficient to provide clonidine for said prolonged time period at a rate that effects such stimulation; means for releasing clonidine from the reservoir at said rate to said predetermined area of skin after the patch is affixed to said predetermined area of skin; and means for affixing the patch to said predetermined area of skin.

A preferred embodiment of the skin patch comprises a sandwich-type laminate of: a backing lamina that is substantially impermeable to clonidine, one face of which forms the top of the bandage; a clonidine reservoir lamina adjacent the opposite face of the backing lamina comprising an amount of clonidine at least equal to that required to provide clonidine for said prolonged time period at an alpha-adrenergic stimulating rate dispersed in a carrier that is permeable to clonidine; a microporous membrane lamina adjacent and below the clonidine reservoir lamina through which the clonidine is released from the reservoir lamina at said rate after the skin patch is affixed to the skin; and a contact adhesive lamina adjacent and below the microporous membrane lamina by which the bandage is affixed to the skin comprising a contact adhesive that is permeable to clonidine and an amount of clonidine that constitutes at least a substantial portion of the quantity of clonidine that is immobilized by said predetermined area of skin.

As used herein the term "effective surface area" means the surface area of the patch that contacts the skin and through which clonidine is administered to the skin. As used herein in connection with describing the constant rate portion of the dosage regimen and the rate at which clonidine is released from said reservoir layer, the term "substantially" indicates that the rate may vary ±30%. Such variation may be inherent in the manufacturing procedure, or be caused by temperature fluctuation, poor affixation of the patch to the skin, and the like. As used herein in connection with describing the magnitude of the priming dose the term "substantial" means at least about 50% and preferably at least about 75%. As used herein the term "prolonged time period" will usually mean a period from 0.5 to 14 days. As used herein the term "clonidine" denotes generally one or more of 2,6-dichloro-N-2-imidazolidinylidene benzeneamine, or benzeneamines structurally and functionally related thereto that are described in U.S. Pat. No. 3,454,701. U.S. Pat. No. 3,454,701 is incorporated herein by reference for its disclosure of such structurally and functionally related benzeneamines. With respect to the preferred embodiments of the invention the term "clonidine" denotes 2,6-dichloro-N-2-imidazolidinylidene benzeneamine. That compound is represented by the structural formula:

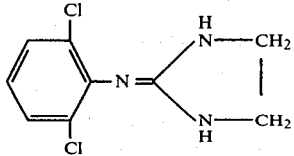

BRIEF DESCRIPTION OF THE DRAWING

The drawing is an enlarged, schematic, cross-sectional view of the preferred embodiment of the skin patch of the invention.

DETAILED DESCRIPTION OF THE PREFERRED EMBODIMENTS

The invention is a result of the discovery that clonidine may be administered transdermally to the systemic circulation to effect alpha-adrenergic stimulation without eliciting intolerable side effects such as excessive dry mouth, drowsiness, and sedation. The skin patch of the invention delivers clonidine to the blood at a substantially constant alpha-adrenergic, stimulating rate optionally preceded by an initial priming dose. The alpha-adrenergic stimulation may be peripheral and/or central. Such stimulation is effective for providing prevention and/or curative hypertension therapy, migraine therapy, glaucoma therapy, or vasoconstrictor therapy or menopausal therapy. For providing therapy for hypertension or migraine the stimulation is primarily central.

A priming dose is included in the dosage program in instances in which it is necessary or desirable to shorten the time it takes for the clonidine concentration in the blood to reach the level required to produce alpha-adrenergic stimulation. It partially does this by "saturating" the skin at the administration site with clonidine. In this respect the skin initially acts as a "sink" rather than as a "conduit", with most of the clonidine initially administered being immobilized within the skin and not passing through to circulation. However, once the skin is "saturated", that is the immobilization sites are occupied, additional clonidine passes through the dermis to be picked up by the capillaries and on into systemic circulation. Thus the amount of clonidine administered in the priming dose is a function of the area of skin being treated. A priming dose of 10 to 300 mcg clonidine per $cm^2$ of skin being treated will usually allow the therapeutic level in the blood to be reached within 12 to 36 hours. In most instances the priming dose will be in the range of 150 to 250 mcg clonidine per $cm^2$ of skin being treated. Alternatively the priming dose may be expressed in terms of the average release rate per unit of effective surface area over the first two hours of administration. Expressed in this manner in most instances the priming dose will be in the range of 75 to 125 $mcg/hr/cm^2$.

If therapy is to be provided past the lifetime of a single patch, successive patches may be applied to the skin to continue therapy. In this regard it may be desirable for such successive patches to deliver a priming dose of equal or less magnitude as the priming dose of the first patch, or perhaps no priming dose at all. In any event the priming dose, if any, in such successive patches should be such as to maintain the concentration of clonidine in the blood at a therapeutic level without substantial fluctuation above or below that level. Accordingly the priming dose delivered by such successive patches will be on the order of 0 to 300 $mcg/cm^2$ of skin being treated.

The concentration of clonidine in the blood that effects alpha-adrenergic stimulation is estimated to vary between 0.1 and 15 ng/ml, usually between 0.2 and 3 ng/ml, depending upon the person being treated. The purpose of administering clonidine transdermally at a substantially constant rate is to supplement the priming dose, if any, in delivering enough clonidine to reach such a blood concentration and to maintain such a concentration for as long as necesssary. It follows that the constant rate administration will proceed for as long as therapy is required. Substantially constant rates in the range of about 0.1 to about 100 mcg/hr, usually about 0.2 to about 70 mcg/hr will maintain the concentration of clonidine in the blood at a therapeutic level.

The skin location at which the patch is affixed is important. This is because the histology, thickness and vascularization of skin varies from individual to individual as well as from body site to body site on a given individual, and such variance affects the efficacy with which clonidine may be delivered transdermally to the blood. This variance may be substantially eliminated in either of two ways. The first way is to affix the patch at a skin site, namely the mastoidal area, where clonidine permeation appears not to vary significantly from individual to individual and thus the quantity of clonidine delivered to the blood or the rate at which such delivery is made is not significantly different between individuals. The second way is to eliminate the stratum corneum as a quantity-affecting or rate-affecting element by treating the skin at the administration site with a skin permeation enhancing agent. Such treatment will allow the patch to be used at body sites, such as the arms, legs or torso, other than the mastoidal area. Depending on the particular agent involved, the treatment may occur prior to or simultaneously with the administration of clonidine. Likewise, the quantity of agent needed will depend on the particular agent used. In any event, the agent plays the dual role of increasing the permeability of the stratum corneum to clonidine and decreasing the tendency of the stratum corneum to bind or immobilize clonidine. Examples of known agents which may be used are dodecyl pyrrolidone, dimethyl lauramide and dimethyl sulfoxide. All three of these agents may be used in pre-treatment applications. The pyrrolidone and lauramide may be applied to the administration site at about 4 to 8 $mg/cm^2$ for approximately an hour and then washed off.

The drawing depicts a therapeutic system in the form of a skin patch, generally designated 10, that when applied to skin administers clonidine in an initial priming dose and then at a substantially constant rate. Patch 10 is a five-layer laminate. The top layer 11 is a backing that is substantially impermeable to clonidine. Its face 12 forms the top surface of the patch. Backing 11 serves as a protective covering, keeps the volatile components of the patch from escaping, and fulfills a support function. Preferably, backing layer 11 is itself a laminate of films of polymer and metal foil such as aluminum foil. Polymers that may be used in the layer are high and low density polyethylene, polypropylene, polyvinylchloride and polyethylene terephthalate.

Below and adjacent to layer 11 is a clonidine reservoir layer 13. Layer 13 contains about 1 to about 6 mg of clonidine, the undissolved portion of which is depicted as particles 14. The clonidine contained in layer 13 is delivered to the blood during the constant administration portion of the dosage program. Particles 14 are dispersed homogeneously in a gelled mixture of an organic, apolar, nonvolatile inert liquid, such as mineral oil of about 10 to about 100 cp at 25° C., and a blend of polyisobutenes. The inert liquid will usually constitute 35% to 65% by weight of the mixture and the polyisobutene will correspondingly usually constitute 35% to 65% by weight of the mixture. The polyisobutene blend comprises a low molecular weight polyisobutene (35,000-50,000 viscosity average molecular weight) and a high molecular weight polyisobutene (1,000,000-1,500,000 viscosity average molecular weight). Preferred mixtures comprise 35% to 65% mineral oil, 10% to 40% low molecular weight polyisobutene, and 10% to 40% high molecular weight polyisobutene. These oil-polyisobutene mixtures are excellent adhesives and help to hold the patch together. If they were not good adhesives, other means, such as heat sealing, could be considered to keep the patch together.

The inert liquid (mineral oil) in layer 13 functions as a carrier for the clonidine. It is preferable that the inert liquid be one in which clonidine has limited solubility (for instance, its solubility in mineral oil is approximately 0.5 mg/ml) and the relative amounts of each in layer 13 be such that the inert liquid is saturated with the clonidine for essentially the entire dispensing lifetime of the patch.

The next lamina in the patch is a microporous membrane 15 whose pores are filled with the above described inert liquid. Membrane 15 is the element of the patch that controls the rate at which the clonidine is released from layer 13. The flux of clonidine through membrane 15 and the area of membrane 15 must be such that clonidine is released from reservoir layer 13 to the skin at a substantially constant rate in the range of 0.1 to 100 mcg/hr after the patch has been put in use. The flux follows Fick's law. It is a function of the tortuosity, porosity and thickness of the membrane, the concentration gradient of clonidine across the membrane and the diffusion coefficient of clonidine in the inert liquid. The concentration gradient depends on the clonidine concentrations in the inert liquid at the opposite sides of the membrane. The diffusion coefficient depends on the inert liquid viscosity and decreases with increasing viscosity. The three properties of the membrane are, of course, constant for any given membrane. Membranes that have porosities from about 0.1 to 0.85, tortuosities from 1 to 10, and thicknesses from $10^{-3}$ to $10^{-2}$ cm may be used. The membrane may be formed from polymers such as a polypropylene, polytetrafluorethylene, polycarbonates, polyvinylchloride, polyviylchloride, cellulose acetate, cellulose nitrate, and polyacrylonitrile.

Below and adjacent membrane 15 is a contact adhesive lamina 16. Lamina 16 contains 10 to 300 mcg clonidine per $cm^2$ effective surface area. The undissolved portion of the clonidine is depicted as particles 17. The clonidine in lamina 16 is administered as the priming dose in the invention method. The clonidine is dispersed homogeneously in the same inert liquid polyisobutene mixture that is used in layer 13. Lamina 16 is the means by which the patch is attached to the skin. In this regard the inert liquid-polyisobutene mixture adheres less strongly to skin than it does to the other laminas of the patch; therefore, the patch tends to remain intact when it is pulled off the skin.

Prior to use, the patch also includes a strippable, protective coating 18 that covers lamina 16. Just prior to use, coating 18 is peeled away from lamina 16 and discarded. It may be made from clonidine-inert liquid impermeable materials such as the polymers from which backing 11 may be made, with the provision that these materials are made strippable, such as by siliconizing.

Patch 10 may be made in the following manner. The composition for forming layer 13 is made by mixing homogenously clonidine, the inert liquid and a liquid that is a nonsolvent for clonidine but a solvent for the polyisobutene. Low molecular weight hydrocarbon solvents such as heptane, hexane, and cyclohexane may be used. The mixing should be done at a high shear to ensure proper clonidine particle size in the layer. Particle size affects the dissolution rate of clonidine in the other components of the layer and the adhesive properties of the layer. Particle sizes in the range of about 5 to 20 microns (number average diameter) are acceptable. The mixture of high and low molecular weight polyisobutenes is then mixed in using a low shear mixing means such as a magnetic stirrer or rotating wheel until the clonidine particles are suspended and the polyisobutenes are dissolved. The relative proportions of clonidine, inert liquid, and polyisobutene in this composition are stated above. The composition for forming contact adhesive layer 16 is made in the same manner as the composition for layer 13 using an appropriate adjustment in the proportions of the ingredients. The number average diameter of the clonidine particles may be determined from measurements of their specific surface area according to the empirically derived equation:

$$d=(6/A\rho)$$

wherein d is the number average diameter, $\rho$ is the density of clonidine and A is the specific surface area. S. Brunauer, B. Emmett, E. Teller, J. Am. Chem. Soc. 60, 309 (1938); S. Gregg, "The Surface Chemistry of Solids", 2nd ed., Reinhold Publishing Corp., N.Y. (1961); S. Gregg and K. Sing, "Adsorption, Surface Area and Porosity", Academic Press, N.Y. (1967); D. Yound and A. Crowell, "Physical Adsorption of Gases", Butterworth and Co. Ltd., London (1962); C. Orr and J.M. Dalla Valla, "Fine Particle Measurements", Macmillian, N.Y. (1959).

The reservoir layer composition is then cast onto one face of backing layer 11 and allowed to dry to form layer 13. Similarly, the contact adhesive layer composition is cast onto one face of strippable coating layer 18 and allowed to dry to form layer 16. The reservoir layer-backing layer assembly is then laminated to one face of microporous membrane layer 15 (saturated with the inert liquid) and the contact adhesive layer-strippable coating layer assembly is laminated to the other face of membrane layer 15. The resulting laminate is usually made in large sheets from which individual patches 10 of the desired size and shape may be cut or punched.

Patch 10 may be applied to either mastoidal region and it will administer clonidine according to the described dosage program without requiring any prior or simultaneous treatment of the region with a skin permeation enhancing agent. As indicated above, if the patch is applied to a body site other than a mastoidal area, the site should be treated with one or more of the described skin permeation enhancing agents. If simultaneous treatment is desired, the agent may be incorporated into patch 10. In that instance, layers 13 and 16 will contain effective quantities of such agent.

It has also been found fortuitously that clonidine is not irritating to the skin and that it has a local microbiocidal effect. Thus no additional biocidal agent need be used to inhibit organism growth at the occluded skin site.

The size of the patch is not critical. The patch will usually be sized to administer clonidine to an area of skin in the range of 0.5 to 10 cm$^2$. Correlatively, the effective surface area of the patch will also usually be in the range of 0.5 to 10 cm$^2$.

EXAMPLE

The following example illustrates the invention. It is not intended to limit the scope of the invention in any way. Unless indicated otherwise, parts are by weight.

A slurry of 2.9 w/w% 2,6-dichloro-N-2-imidazolidinylidene benzeneamine, 10.4 w/w% mineral oil (10 cp @ 25° C.), and 75 w/w% heptane was prepared. The slurry was homogenized for 10 minutes @ 5000–10000 rpm in a Polytron homogenizer. A mixture of 5.2 w/w% of high molecular weight polyisobutene (sold under the designation Vistanex MML-100, 1,200,000 viscosity average molecular weight) and 6.5 w/w% of low molecular weight polyisobutene (sold under the designation Vistanex LM-MS, 35,000 viscosity average molecular weight) was then added to the homogenized slurry and mixed at low shear until the benzeneamine particles were suspended and the polyisobutenes were dissolved. The resulting mixture was cast onto a 100 micron thick backing film of aluminized polyethylene terephthalate (sold under the designation MEDPAR), allowed to air dry overnight and then oven dried for 15 minutes @ 60° C. to form a clonidine reservoir layer approximately 50 microns thick.

A contact adhesive layer-strippable coating combination was similarly prepared by casting a similarly prepared mixture of 0.9 w/w% of the benzeneamine, 11.4 w/w% of said mineral oil, 75 w/w% heptane, 5.7 w/w% of said high molecular weight polyisobutene, and 7 w/w% of said low molecular weight polyisobutene onto a 125 micron thick siliconized, aluminized, polyethylene-backed polyethylene terephthalate film. The combination was about 175 microns thick.

The above described contact adhesive layer-strippable coating layer combination is then laminated to one face of a 25 micron thick microporous polypropylene membrane (sold under the designation Celgard 2400) saturated with said mineral oil and the above described backing layer-benzeneamine reservoir layer combination is laminated to the opposite face of the membrane. Circular, disc-shaped skin patches, 1.1 cm$^2$ in area, are punched from the resulting 5-layer laminate.

In vitro tests of the patches indicated they released an initial priming dose of 60 mcg of the benzeneamine (average over the first two hours) followed by an essentially constant dosage of 3 mcg/hr (average over 168 hours). In vivo tests gave release rates essentially equivalent to those obtained in the in vitro tests.

Modifications of the above described therapeutic systems that are within the skill of the medical, chemical and/or pharmaceutical arts are intended to be within the scope of the following claims.

We claim:

1. A therapeutic system in the form of a skin patch for administering clonidine continuously and transdermally through a predetermined area of unbroken skin in a controlled manner for a prolonged time period to effect central alpha-adrenergic stimulation comprising:
   (a) a backing that is substantially impermeable to clonidine, one face of which forms the top of the patch;
   (b) a clonidine reservoir adjacent the opposite face of the backing that contains an amount of clonidine sufficient to provide clonidine for said prolonged time period at a central alpha-adrenergic stimulating rate;
   (c) means for releasing clonidine from the reservoir at said rate to said predetermined area of skin; and
   (d) means for affixing the patch to said predetermined area of skin.

2. The therapeutic system of claim 1 wherein the central alpha-adrenergic stimulating rate is one that provides hypertension therapy.

3. A therapeutic system in the form of a skin patch for administering 2,6-dichloro-N-2-imidazolidinylidene benzeneamine continuously and transdermally through a predetermined area of unbroken skin in a controlled manner for a prolonged time period to effect central alpha-adrenergic stimulation comprising a sandwich-type laminate of:
   (a) a backing lamina that is substantially impermeable to the benzeneamine, one face of which forms the top of the patch;
   (b) a benzeneamine reservoir lamina adjacent the opposite face of the backing lamina comprising:
      (i) an amount of said benzeneamine at least equal to that required to provide said benzeneamine for said prolonged time period at a central alpha-adrenergic stimulating rate, dispersed in
      (ii) a carrier that is permeable to said benzeneamine;
   (c) a microporous membrane lamina adjacent and below the benzeneamine reservoir lamina through which the benzeneamine is released from the reservoir lamina at said rate after the skin patch is affixed to the skin; and
   (d) a contact adhesive lamina adjacent and below the microporous membrane lamina by which the patch is affixed to the skin comprising:
      (i) a contact adhesive that is permeable to the benzeneamine; and
      (ii) an amount of benzeneamine that constitutes at least a substantial portion of the quantity of the benzeneamine that is immobilized by said predetermined area of skin.

4. The therapeutic system of claim 3 wherein the rate is one that provides hypertension therapy.

5. The therapeutic system of claim 4 wherein said rate is in the range of 0.1 to 100 mcg/hr and said amount of benzeneamine in said contact adhesive lamina is 10 to 300 mcg/cm$^2$ of said predetermined area of skin.

6. The therapeutic system of claim 4 wherein said rate is in the range of 0.2 to 70 mcg/hr and said amount of benzeneamine in the contact adhesive lamina is 150 to 250 mcg/cm$^2$ of said predetermined area of skin.

7. The therapeutic system of claim 4 including:
   (e) a strippable coating lamina adjacent and below the contact adhesive lamina that is substantially impermeable to the components of the contact adhesive lamina and is adapted to be stripped off the patch before the patch is affixed to the skin.

8. The therapeutic system of claim 4 wherein the carrier and the contact adhesive comprise a gelled mixture of mineral oil of about 10 to about 100 cp at 25° C. and polyisobutene.

9. The therapeutic system of claim 8 wherein the polyisobutene is a blend of a first polyisobutene having a viscosity average molecular weight of 35,000 to 50,000 and a second polyisobutene having a viscosity average molecular weight of 1,000,000 to 1,500,000.

10. The therapeutic system of claim 9 wherein the mineral oil constitutes 35% to 65% by weight of the gelled mixture, the first polyisobutene constitutes 10% to 40% by weight of the gelled mixture and the second polyisobutene constitutes 10% to 40% by weight of the gelled mixture.

11. The therapeutic system of claim 4 wherein the microporous membrane lamina has a porosity of about 0.1 to 0.85, a tortuosity of about 1 to 10 and a thickness of about $10^{-3}$ to $10^{-2}$ cm.

12. The therapeutic system of claim 11 wherein the microporous membrane lamina is made of polypropylene.

13. The therapeutic system of claim 12 wherein the backing layer is made of aluminized polyethylene terephthalate.

14. The therapeutic system of claim 4 including:
(e) a strippable coating lamina adjacent and below the contact adhesive lamina that is substantially impermeable to the components of the contact adhesive lamina and is adapted to be stripped off the patch before the patch is affixed to the skin, and wherein said rate is in the range of 0.2 to 70 mcg/hr, the amount of the benzeneamine in the contact adhesive lamina is 150 to 250 mcg/cm$^2$ of skin, the particle size of the undissolved benzeneamine present in the reservoir lamina and contact adhesive lamina being in the range of about 5 to 20 microns, the carrier comprises a gelled mixture of 35% to 65% by weight mineral oil of about 10 to about 100 cp at 25° C., 10% to 40% by weight polyisobutene having a viscosity average molecular weight of 35,000 to 50,000, and 10% to 40% by weight polyisobutene having a viscosity average molecular weight of 1,000,000 to 1,500,000, the contact adhesive is made of said gelled mixture, the microporous membrane lamina is made of polypropylene, and the backing layer is made of aluminized polyethylene terephthalate.

* * * * *